US00PP17037P2

(12) United States Plant Patent
Dümmen

(10) Patent No.: US PP17,037 P2
(45) Date of Patent: Aug. 22, 2006

(54) ***GERANIUM* PLANT NAMED 'DUEMELLINA'**

(50) Latin Name: *Pelargonium×hortorum*
Varietal Denomination: Duemellina

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/171,806

(22) Filed: Jun. 30, 2005

(51) Int. Cl.
*A01H 5/00* (2006.01)

(52) U.S. Cl. ..... Plt./325

(58) Field of Classification Search ..... Plt./325, Plt./328, 329

See application file for complete search history.

*Primary Examiner*—Kent Bell
(74) *Attorney, Agent, or Firm*—C. A. Whealy

(57) ABSTRACT

A new and distinct cultivar of Zonal *Geranium* plant named 'Duemellina', characterized by its upright, somewhat outwardly spreading and rounded plant habit; freely branching habit; freely and early flowering habit; and light red purple-colored semi-double flowers with red purple-colored spots.

1 Drawing Sheet

Botanical denomination: *Pelargonium×hortorum.*
Cultivar designation: 'Duemellina'.

BACKGROUND OF THE INVENTION

The present invention relates to a new and distinct cultivar of Zonal *Geranium* plant, botanically known as *Pelargonium×hortorum*, and hereinafter referred to by the name 'Duemellina'.

The new Zonal *Geranium* is a product of a planned breeding program conducted by the Inventor in Rheinberg, Germany. The objective of the breeding program was to develop new freely and early flowering Zonal *Geraniums* with attractive flower and foliage colors.

The new Zonal *Geranium* originated from a cross-pollination made by the Inventor in May, 1999, of an unnamed proprietary selection of *Pelargonium×hortorum*, not patented, as the female, or seed, parent with a proprietary selection of *Pelargonium×hortorum* identified as code number F-02-05, not patented, as the male, or pollen, parent. The cultivar Duemellina was discovered and selected by the Inventor as a flowering plant within the progeny from this cross-pollination in a controlled environment in Rheinberg, Germany in May, 2003.

Asexual reproduction of the new cultivar by terminal vegetative cuttings at Rheinberg, Germany since May, 2003, has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Duemellina'. These characteristics in combination distinguish 'Duemellina' as a new cultivar and distinguish it from other known Zonal *Geranium* cultivars:

1. Upright, outwardly spreading and rounded plant habit.
2. Freely branching habit.
3. Freely and early flowering habit.

4. Light red purple-colored semi-double flowers with red purple-colored spots.

Compared to plants of the parent selections, plants of the new Zonal *Geranium* differ in flower coloration. In addition, plants of the new Zonal *Geranium* are stronger than plants of the parent selections.

The new Zonal *Geranium* can be compared to plants of the cultivar SEL Lesmona, not patented. In side-by-side comparisons conducted in Rheinberg, Germany, plants of the new Zonal *Geranium* differed from plants of the cultivar SEL Lesmona in the following characteristics:

1. Plants of the new Zonal *Geranium* were more compact than plants of the cultivar SEL Lesmona.
2. Plants of the new Zonal *Geranium* had smaller leaves and longer leaf petioles than plants of the cultivar SEL Lesmona.
3. Plants of the new Zonal *Geranium* and the cultivar SEL Lesmona differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Duemellina' grown in a container.

DETAILED BOTANICAL DESCRIPTION

The cultivar Duemellina has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium×hortorum* cultivar Duemellina.

Parentage:

*Female parent.*—Unnamed proprietary selection of *Pelargonium×hortorum*, not patented.

*Male parent.*—Proprietary selection of *Pelargonium×hortorum* identified as F-02-05, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine, fibrous; white in color.

*Rooting habit.*—Freely branching.

Plant description:

*General appearance.*—Upright, somewhat outwardly spreading and rounded plant habit; densely foliated.

*Growth and branching habit.*—Moderately vigorous. Freely branching, about four lateral branches per plant.

*Plant height.*—About 20 cm.

*Plant width.*—About 23 cm.

*Lateral branches.*—Length: About 6.1 cm. Internode length: About 1 cm. Texture: Smooth, glabrous. Color: 144A.

*Foliage description.*—Arrangement: Alternate, single. Length: About 5.3 cm. Width: About 6.3 cm. Shape: Reniform. Apex: Rounded. Base: Cordate. Margin: Crenate. Venation pattern: Palmate. Texture, upper and lower surfaces: Smooth, glabrous. Color: Developing and fully expanded foliage, upper surface: 137A to 137B. Developing and fully expanded foliage, lower surface: 138A to 138B. Venation, upper surface: 138A to 138B. Venation, lower surface: 144B. Zonation pattern: 144A in color; about 2 mm in width. Petiole: Length: About 5.4 cm. Diameter: About 2 mm. Texture, upper and lower surfaces: Smooth. Color, upper and lower surfaces: 144A.

Flower description:

*Flower arrangement.*—Light red purple-colored semi-double flowers with red purple-colored spots arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about eight flower umbels with about 20 to 25 flowers per umbel.

*Flowering season.*—Flowering continuous spring until the autumn. Plants begin flowering about eight weeks after planting.

*Flower longevity.*—Flowers last about five to seven days on the plant.

*Umbel size.*—Diameter: About 9 cm. Height: About 6 cm.

*Flower size.*—Diameter: About 4.5 cm. Depth (height): About 1.8 cm.

*Flower buds.*—Length: About 1.1 cm. Diameter: About 6 mm. Shape: Ovoid. Color: 144A.

*Petals.*—Quantity per flower: About five. Length: About 2.6 cm. Width: About 2.2 cm. Shape: Obovate. Apex: Rounded. Base: Attenuate. Margin: Entire; sinuate. Texture, upper and lower surfaces: Smooth. Color: When opening and fully opened, upper surface: 67B; spots, 61A to 61B. When opening and fully opened, lower surface: 75B.

*Petaloids.*—Quantity per flower: About six to eight. Length: About 2.1 cm. Width: About 1.4 cm. Shape: Obovate. Apex: Rounded. Base: Attenuate. Margin: Entire; sinuate. Texture, upper and lower surfaces: Smooth. Color: When opening and fully opened, upper surface: 67B; spots, 61A to 61B. When opening and fully opened, lower surface: 75B.

*Sepals.*—Quantity per flower: About five arranged in a single whorl. Length: About 1.1 cm. Width: About 3.8 mm. Shape: Elongated, tapering. Apex: Apiculate. Margin: Entire. Texture, upper and lower surfaces: Smooth; glabrous. Color, upper and lower surfaces: 144A to 144B.

*Peduncle* (*umbel stem*).—Length: About 13.1 cm. Diameter: About 1.5 cm. Angle: Mostly erect. Strength: Moderately strong. Texture: Smooth; glabrous. Color: 144A.

*Pedicel* (*individual flower stem*).—Length: About 3 cm. Diameter: About 1 mm. Angle: Mostly erect. Strength: Moderately strong. Texture: Pubescent. Color: 144A overlain with 59B.

*Reproductive organs.*—Androecium: Anther quantity per flower: About seven to ten. Anther length: About 2 mm. Anther shape: Ovate. Anther color: 43B. Pollen amount: Moderate. Pollen color: 28A. Gynoecium: Pistil quantity per flower: One. Pistil length: About 1.3 cm. Stigma shape: Five-parted, star-shaped. Stigma color: 59C. Style length: About 3 mm. Style color: 59C. Ovary color: Close to 144A.

*Seed/fruit.*—Development of seeds and fruit have not been observed.

Disease/pest resistance: Plants of the new Zonal *Geranium* have not been observed to be resistant to pathogens and pests common to Zonal *Geraniums*.

Temperature tolerance: Plants of the new Zonal *Geranium* have been observed to be tolerant to temperatures ranging from 5 to 40° C.

It is claimed:

1. A new and distinct cultivar of Zonal *Geranium* plant named 'Duemellina', as herein illustrated and described.

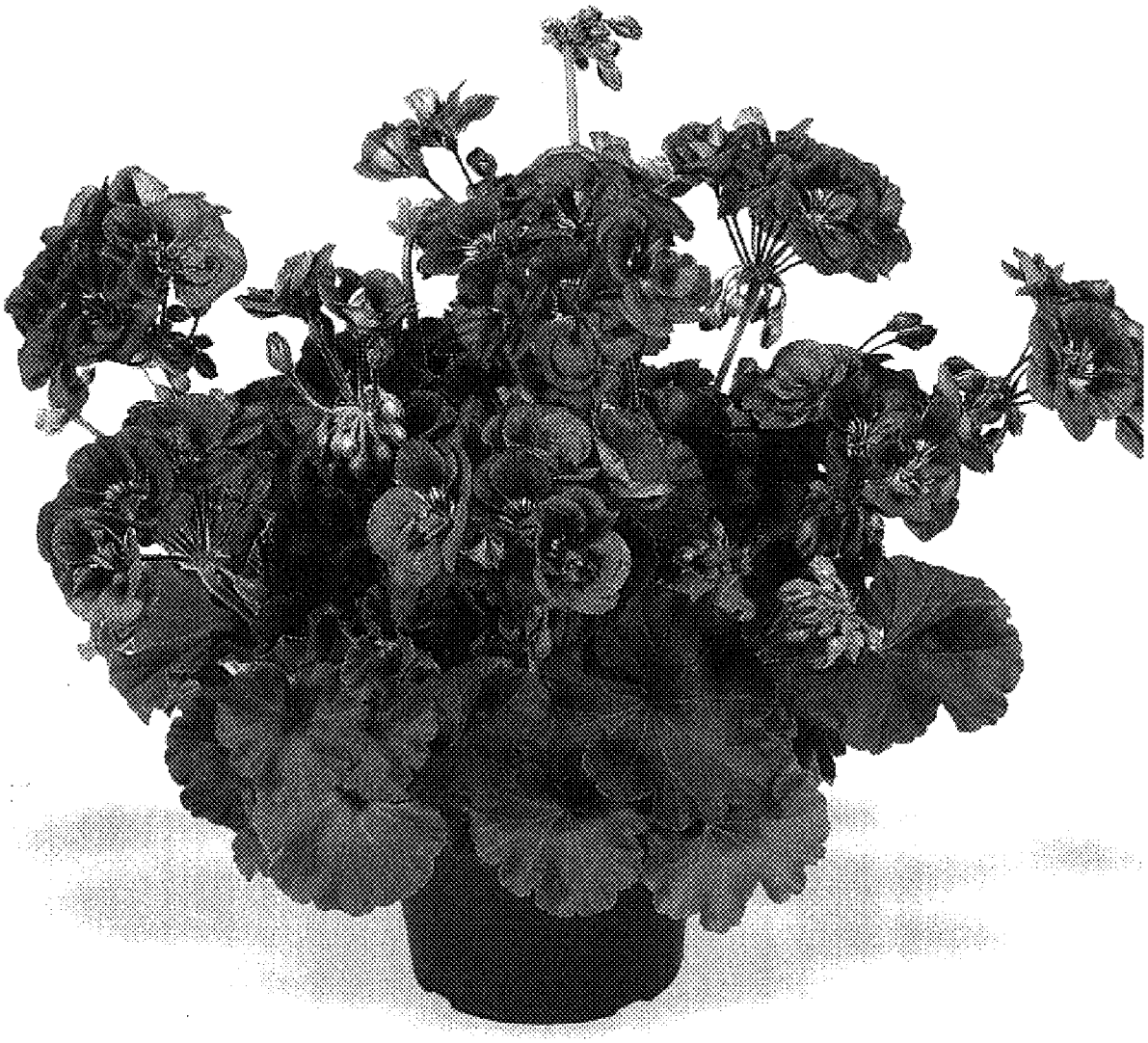

* * * * *